United States Patent
Bats et al.

(10) Patent No.: US 9,707,539 B2
(45) Date of Patent: Jul. 18, 2017

(54) ZEOLITE ADSORBENTS COMPRISING ZEOLITE EMT, PROCESS FOR PREPARING THE SAME AND USES THEREOF

(71) Applicants: IFP ENERGIES NOUVELLES, Rueil-Malmaison (FR); CECA S.A., La Garenne Colombes (FR)

(72) Inventors: Nicolas Bats, Saint Symphorien D'Ozon (FR); Catherine Laroche, Vernaison (FR); Philibert Leflaive, Mions (FR); Ludivine Bouvier, Orthez (FR)

(73) Assignees: IFP ENERGIES NOUVELLES, Rueil-Malmaison (FR); ARKEMA FRANCE, Colombes (FR)

( * ) Notice: Subject to any disclaimer, the term of this patent is extended or adjusted under 35 U.S.C. 154(b) by 0 days.

(21) Appl. No.: 14/888,309

(22) PCT Filed: Apr. 29, 2014

(86) PCT No.: PCT/EP2014/058732
§ 371 (c)(1),
(2) Date: Oct. 30, 2015

(87) PCT Pub. No.: WO2014/177567
PCT Pub. Date: Nov. 6, 2014

(65) Prior Publication Data
US 2016/0067673 A1    Mar. 10, 2016

(30) Foreign Application Priority Data

Apr. 30, 2013    (FR) .................................... 13 53971

(51) Int. Cl.
| | | |
|---|---|---|
| *B01J 20/18* | (2006.01) | |
| *B01J 20/28* | (2006.01) | |
| *B01J 20/30* | (2006.01) | |
| *B01J 20/32* | (2006.01) | |
| *B82Y 30/00* | (2011.01) | |
| *C07C 29/76* | (2006.01) | |
| *C07C 37/82* | (2006.01) | |
| *C07C 7/13* | (2006.01) | |

(52) U.S. Cl.
CPC ......... *B01J 20/186* (2013.01); *B01J 20/2803* (2013.01); *B01J 20/28004* (2013.01); *B01J 20/28007* (2013.01); *B01J 20/3028* (2013.01); *B01J 20/3042* (2013.01); *B01J 20/3071* (2013.01); *B01J 20/3078* (2013.01); *B01J 20/3085* (2013.01); *B01J 20/3204* (2013.01); *B01J 20/3236* (2013.01); *B82Y 30/00* (2013.01); *C07C 7/13* (2013.01); *C07C 29/76* (2013.01); *C07C 37/82* (2013.01)

(58) Field of Classification Search
CPC ............... B01J 20/186; B01J 20/28004; B01J 20/28007; B01J 20/2803; B01J 20/3028; B01J 20/3042; B01J 20/3071; B01J 20/3078; B01J 20/3085; B01J 20/3204; B01J 20/3236; B82Y 30/00; C07C 29/76; C07C 37/82; C07C 7/13
See application file for complete search history.

(56) References Cited

U.S. PATENT DOCUMENTS

| | | | |
|---|---|---|---|
| 2,985,589 | A | 5/1961 | Broughton |
| 3,558,730 | A | 1/1971 | Neuzil |
| 3,558,732 | A | 1/1971 | Neuzil |
| 3,626,020 | A | 12/1971 | Neuzil |
| 3,663,638 | A | 5/1972 | Neuzil |
| 3,960,774 | A | 6/1976 | Rosback |
| 4,402,832 | A | 9/1983 | Gerhold |
| 4,498,991 | A | 2/1985 | Oroskar |
| 5,284,992 | A | 2/1994 | Hotier |
| 5,629,467 | A | 5/1997 | Hotier |
| 6,146,613 | A | 11/2000 | Anglerot |
| 7,452,840 | B2 | 11/2008 | Plee |
| 8,530,367 | B2 | 9/2013 | Bouvier |
| 2009/0326309 | A1 | 12/2009 | Priegnitz |

FOREIGN PATENT DOCUMENTS

| | | |
|---|---|---|
| EP | 0915808 | 5/1999 |
| FR | 2789914 | 8/2000 |
| JP | 2012218998 | 11/2012 |
| NO | 304183 | 11/1998 |
| WO | 9822389 | 5/1998 |
| WO | 2008009845 | 1/2008 |

OTHER PUBLICATIONS

International Search Report for International Application No. PCT/EP2014/058732 mailed Jun. 3, 2014.
Ng, E.P., et al., "Capturing ultrasmall EMT zeolite from template-free systems," Jan. 6, 2012, pp. 70-73, vol. 335(70), Science.
Ng, E.P., et al., "Nucleation and crystal growth features of EMT-type zeolite synthesized from an organic-template-free system," Dec. 21, 2012, pp. 4758-4765, vol. 24(24), Chemistry of Materials.
Ruthven, D. et al., "Principles of adsorption and adsorption processes," 1984, pp. 243, 326, 407, 248-250, John Wiley & Sons.
Sun, J., et al., "Synthesis of zeolite EMT with a novel route promoted by surfactants and its benefit in catalytic performance," 1999, pp. 2459-2460, Issue 24, Journal of the Chemical Society, Chemical Communications.
Written Opinion of the International Searching Authority for International Application No. PCT/EP2014/058732 mailed Jun. 3, 2014.

*Primary Examiner* — Paul A Zucker
*Assistant Examiner* — Mark Luderer
(74) *Attorney, Agent, or Firm* — RatnerPrestia

(57) ABSTRACT

The present invention relates to zeolite adsorbents based on agglomerated crystals of zeolite EMT comprising barium and/or potassium. These adsorbents find applications in the separation of aromatic C8 isomer fractions, especially of xylenes, in the separation of substituted toluene isomers, such as nitrotoluene, diethyltoluene and toluenediamine, and in the separation of cresols, and in the separation of polyhydric alcohols, such as sugars.

22 Claims, No Drawings

ZEOLITE ADSORBENTS COMPRISING ZEOLITE EMT, PROCESS FOR PREPARING THE SAME AND USES THEREOF

CROSS REFERENCE TO RELATED APPLICATIONS

This application is the national phase of International application of PCT/EP2014/058732, filed Apr. 29, 2014, which claims priority from French application 1353971, filed Apr. 30, 2013. The entire disclosure of each of these applications are incorporated herein by reference for all purpose.

TECHNICAL FIELD

The invention relates to adsorbents based on agglomerated crystals of zeolite EMT comprising barium or potassium or barium and potassium, to a process for preparing them and to the uses thereof.

These adsorbents may be used more particularly for the liquid-phase or gas-phase production of very pure para-xylene from an aromatic hydrocarbon feedstock containing isomers containing 8 carbon atoms.

PRIOR ART

It is known in the prior art that adsorbents comprising crystalline aluminosilicates can be used for separating certain hydrocarbons from mixtures containing them. In the field of separating out aromatic hydrocarbons and in particular of separating out aromatic C8 isomers, it is generally acknowledged that the use of particular cations in the cationic sites of crystalline zeolite aluminosilicates improves the selectivity of the zeolite for one of the aromatic C8 isomers. This differentiated adsorption within the zeolite allows the separation of the various aromatic C8 isomers, which is used industrially for the production of very pure para-xylene from an aromatic hydrocarbon feedstock containing isomers containing 8 carbon atoms.

Thus, the use of zeolite adsorbents consisting of zeolites X or Y comprising, besides sodium cations, barium, potassium or strontium ions, alone or as mixtures, for selectively adsorbing in the liquid phase para-xylene in a mixture of aromatic hydrocarbons, is well known from the prior art.

U.S. Pat. Nos. 3,558,730, 3,558,732, 3,626,020, 3,663,638 and 3,960,774 show that zeolite adsorbents comprising aluminosilicates of faujasite (FAU) structure based on sodium and barium or based on sodium, barium and potassium are efficient for separating out para-xylene present in C8 aromatic fractions (fractions comprising aromatic hydrocarbons containing 8 carbon atoms). The above adsorbents are preferably used as adsorption agents in liquid-phase processes, especially of simulated counter-current type, similar to those described in patent U.S. Pat. No. 2,985,589 and which apply, inter alia, to aromatic C8 fractions.

However, in general, the adsorption properties of zeolites for aromatic hydrocarbons containing 8 carbon atoms (xylenes and ethylbenzene) vary very finely as a function of the size and shape of the pores and also of the position of the cations in the structure, which have an influence both on the electrostatic field present within the zeolite and on the shape of the accessible volume in the pores. Other parameters, such as the polarizability of the cations and of the molecules or the flexibility of the structure, may also have an influence. It is thus extremely difficult to predict theoretically and with precision the adsorption characteristics of a zeolite with respect to aromatic hydrocarbons containing 8 carbon atoms.

Thus, for example, to improve the adsorption selectivity of zeolites having the faujasite structure for aromatic C8 isomers, numerous studies have mentioned the influence of the Si/Al ratio of the zeolite, the nature of the exchange cations, and also their water content. However, it is very difficult to predict the degree of improvement since these factors exert combined actions on the adsorption characteristics of the zeolites.

The important factors that influence the performance qualities of a process for separation by adsorption especially include the adsorption selectivity, the adsorption capacity and the matter transfer kinetics which defines the rates of adsorption and desorption of the various compounds. The adsorbent must therefore have good matter transfer properties so as to ensure a number of theoretical plates that is sufficient to achieve efficient separation of the species in mixture, as indicated by Ruthven in the publication entitled "Principles of Adsorption and Adsorption Processes", John Wiley & Sons (1984), pages 326 and 407. Ruthven indicates (ibid., page 243) that, in the case of an agglomerated adsorbent, the overall matter transfer depends on the addition of the intracrystalline diffusional resistance and of the intercrystal diffusional resistance. The intracrystalline diffusional resistance is proportional to the square of the radii of the crystals and inversely proportional to the diffusivity of the intracrystalline molecules.

The intercrystal diffusional resistance (also known as macropore resistance) is itself proportional to the square of the radii of the agglomerates and inversely proportional to the diffusivity of molecules in the macropores. For a given zeolite structure, a given agglomerate size and a given operating temperature, the diffusivities are set, and the only means for improving the matter transfer consists in reducing the diameter of the crystals. A gain on the overall transfer will thus be obtained by reducing the size of the crystals.

To estimate this improvement in the transfer kinetics, use may be made of the plate theory described by Ruthven in "Principles of Adsorption and Adsorption Processes" (ibid., pages 248-250). This approach is based on the representation of a column by a finite number of ideally stirred hypothetical reactors (theoretical stages). The equivalent height of theoretical plates is a direct measurement of the axial dispersion and of the matter transfer resistance of the system.

Consequently, a person skilled in the art expects agglomerated zeolite adsorbents that have both good capacity for adsorbing xylenes and good selectivity for para-xylene to have very good properties for separating out xylenes when they are prepared from small zeolite crystals in liquid-phase processes for separating out para-xylene contained in aromatic C8 fractions, for example of simulated counter-current type. A person skilled in the art, however, finds it impossible to define in principle or theoretically and with precision the adsorption characteristics of a particular zeolite, especially with regard to aromatic hydrocarbons containing 8 carbon atoms.

The synthesis of zeolites leads to crystals (generally in the form of powder) whose use at the industrial scale is particularly difficult (substantial losses of feedstocks during handling). The agglomerated forms of these crystals, in the form of grains, threads and other agglomerates, are therefore preferred, these said forms being able to be obtained by extrusion, pelletizing, and other agglomeration techniques known to those skilled in the art. These agglomerates do not have the inherent drawbacks of pulverulent materials.

These agglomerates, whether they are in the form of platelets, beads, extrudates or the like, generally consist of zeolite crystals, which constitute the active element (in the sense of adsorption), and of a binder for ensuring the cohesion of the crystals in the form of agglomerates and for giving them sufficient mechanical strength to withstand the vibrations and movements to which they are subjected in the course of the operations for separation of the isomers of aromatic C8 fractions.

However, the adsorption properties of these agglomerates are obviously reduced relative to the crystal powder, on account of the presence of agglomeration binder that is inert with respect to adsorption.

Various means have already been proposed for overcoming this drawback of the agglomeration binder of being inert as regards the adsorption performance, among which is the transformation of all or of at least part of the agglomeration binder into zeolite that is active from the adsorption viewpoint. This operation is now well known to those skilled in the art, for example under the name "zeolitization". To perform this operation easily, use is made of zeolitizable binders, which are usually clays belonging to the kaolinite family, and preferably precalcined at temperatures generally between 500° C. and 700° C.

Patent application FR 2 789 914 describes, for example, a process for manufacturing zeolite X agglomerates, with an Si/Al ratio of between 1.15 and 1.5, containing barium and optionally potassium. The agglomerates thus obtained, after zeolitization of the binder, have, from the viewpoint of adsorption of the para-xylene contained in aromatic C8 fractions, improved properties relative to adsorbents prepared from the same amount of zeolite X and of binder, but whose binder is not zeolitized.

Independently, the synthesis of zeolite EMT crystals is also well known from the prior art. Specifically, since the original studies by Guth et al. (F. Dougnier, J. Patarin, J.-L. Guth and D. Anglerot, *Zeolites*, 12, 160 (1992)), numerous studies have been devoted to the synthesis of zeolites having this crystalline structure. The synthesis of pure zeolite EMT is especially possible by using a structuring agent (structure-directing agent or template) such as 18-crown-6 ether and by suitably controlling the synthetic parameters (EP 0 915 808 and JP 201 2/21 8 998).

Numerous studies have been reported in the literature in order to reduce the consumption of crown ether, for example by recycling after the synthesis (F. Dougnier and J. L. Guth, *Microporous Mater.*, 6, 79 (1996)), or using alternative approaches (see, for example, patent NO 964988) and the following publications: R. Wendelbo, M. Stöcker, H. Junggreen, H. B. Mostad and D. E. Akporiaye, *Microporous Mesoporous Mater.*, 28, 361 (1999); M. Matsukata, K. Kizu, M. Ogura and E. Kikuchi, *Cryst. Growth Des.*, 1, 509 (2001); J. Sun, M. Sun, C. Nie and Q. Li, *J. Chem. Soc. Chem. Commun.*, 2459 (1999); and T. Chatelain, J. Patarin, M. Soulard, J. L. Guth and P. Shulz, *Zeolites*, 15, 90 (1995). More recently, studies performed by Mintova et al. (*Chem. Mater.* (2012), 24, 4758-4765; and *Science*, January 2012, 335, 70-73) have demonstrated the possibility of obtaining zeolite EMT crystals without using an organic structuring agent. In addition, features of the crystals obtained are an Si/Al ratio of between 1.0 and 1.4 and also a nanometric size (typically between 6 and 15 nm), which was not the case for the preceding syntheses, 18-crown-6 ether instead stimulating the crystallization of EMT crystals of micrometric size.

The aim of the present invention is to provide novel adsorbents based on zeolite EMT exchanged with barium or potassium, or with barium and potassium, combining:
good selectivity,
good matter transfer and
good adsorption capacity,
for the separation of para-xylene contained in aromatic C8 fractions in a process of simulated counter-current type.

It has in point of fact been found, surprisingly, that good adsorption capacity, good matter transfer and good selectivity for para-xylene can be obtained with adsorbents based on zeolite EMT exchanged with barium or with potassium or with barium and potassium. It is moreover pointed out that the terms "of between . . . and . . . " and "from . . . to . . . " used in the present description should be understood as including each of the limits mentioned, unless otherwise indicated.

SUMMARY OF THE INVENTION

The invention relates to a zeolite adsorbent comprising zeolite EMT crystals and comprising barium and/or potassium, in which the total content of alkali metal or alkaline-earth metal ions oxides other than barium oxide BaO and potassium oxide $K_2O$ is between 0 and 5%, preferably between 0 and 2% and very preferably between 0 and 1% by weight, limits included, relative to the total mass of the adsorbent.

The zeolite EMT crystals advantageously have an Si/Al atomic ratio between 1.00 and 2.00, preferably between 1.0 and 1.50, more preferably between 1.05 and 1.50 and even more preferably between 1.10 and 1.50, limits included.

The number-average diameter of the zeolite EMT crystals is advantageously between 5 nm and 1500 nm, preferably between 5 nm and 1000 nm and even more preferably between 10 nm and 500 nm, limits included.

The adsorbent according to the invention may also comprise crystals of at least one other zeolite, chosen from zeolites of FAU structure, especially LSX, MSX, X, Y or EMC-1, or chosen from zeolites of LTA or MFI structure.

In one embodiment, the said other zeolite(s) are chosen from zeolites of FAU structure, alone or as a mixture, preferably from zeolites X, and the mass fraction of zeolite EMT is between 1 and 50%. In another embodiment, the mass fraction of zeolite EMT may be greater than 50% relative to the total weight of adsorbent, and preferably greater than 80%. The adsorbent according to the invention may also comprise zeolite phases of EMT-FAU intergrowth.

More particularly, the adsorbent according to the invention may have the following characteristics:
the barium content (expressed as the weight percentages of barium oxide BaO) is greater than 10%, preferably greater than 15%, very preferably greater than 18%, even more preferably greater than 23%, or even greater than 33% by weight relative to the total mass of the adsorbent. Advantageously, the barium content is between 23% and 40%, limits included, and typically between 33% and 40%,
the potassium content (expressed as the weight percentages of potassium oxide $K_2O$) is between 0 and 25%, preferably between 0 and 15%, even more preferably between 0 and 5% and very preferably from 0 to 2% by weight relative to the total mass of the adsorbent.

The loss on ignition of the adsorbent according to the invention, measured at 950° C. according to standard NF EN 196-2, is advantageously between 0 and 7.7%, preferably between 4.5 and 6.5% and very preferably between 4.8 and 6% by weight.

The number-average diameter of the adsorbent according to the invention may be between 0.2 mm and 2 mm, in particular between 0.4 mm and 0.8 mm and preferably between 0.4 mm and 0.65 mm, limits included.

The invention also relates to a process for preparing an adsorbent as described above, comprising at least the steps of:
 a) agglomeration of a zeolite powder comprising zeolite EMT with a binder and forming, followed by drying and calcination,
 b) cationic exchange of the agglomerate by placing in contact with a solution of barium ions, or of potassium ions, or of barium ions and potassium ions,
 c) optional cationic exchange with potassium,
 d) followed by washing and drying of the product thus treated, and
 e) activation of the zeolite adsorbent thus obtained.

The preparation process may comprise at least the steps of:
 a) agglomeration of a zeolite powder comprising zeolite EMT with a binder containing at least 80%, preferably at least 90% and more preferably at least 95% by weight of zeolitizable clay and a source of silica, and forming, followed by drying and calcination,
 b) zeolitization of the said zeolitizable binder by the action of an alkaline basic solution, preferably with a solution with a concentration of between 0.5 M and 5 M and for a time of between a few tens of minutes and a few hours, preferably between about 1 hour and 8 hours,
 c) cationic exchange of the agglomerate by placing in contact with a solution of barium ions, or of potassium ions, or of barium ions and potassium ions,
 d) optional cationic exchange with potassium,
 e) followed by washing and drying of the product thus treated, and
 f) activation of the zeolite adsorbent thus obtained.

The invention also relates to an adsorbent as described previously, which may be obtained according to the above preparation process.

The invention also relates to the use of the said adsorbent according to the invention in processes of:
 separation of aromatic C8 isomer fractions and especially of xylenes,
 separation of substituted toluene isomers, such as nitrotoluene, diethyltoluene, toluenediamine, and the like,
 separation of cresols,
 separation of polyhydric alcohols,
and especially for the separation of para-xylene from aromatic isomer fractions containing 8 carbon atoms.

The invention also relates to a process for recovering para-xylene from aromatic hydrocarbon isomer fractions containing 8 carbon atoms, in the liquid phase, by adsorption of para-xylene using the said adsorbent according to the invention in the presence of a desorbent, preferably chosen from toluene and para-diethylbenzene.

The said process may be of the simulated mobile bed type, preferably of simulated counter-current type.

The invention also relates to a process for recovering para-xylene from aromatic hydrocarbon isomer fractions containing 8 carbon atoms, in the gas phase, by adsorption of para-xylene using the said adsorbent according to the invention in the presence of a desorbent, preferably chosen from toluene and para-diethylbenzene.

The invention also relates to a process for separating polyhydric alcohols using the said adsorbent according to the invention.

The invention also relates to a process for separating substituted toluene isomers, such as nitrotoluene, diethyltoluene or toluenediamine, using the said adsorbent according to the invention.

Finally, the invention relates to a process for separating cresols using the said adsorbent according to the invention.

DETAILED DESCRIPTION OF THE INVENTION

A first subject of the present invention is thus zeolite adsorbents based on zeolite EMT. These adsorbents are particularly suitable for use in a process for separating out para-xylene in the liquid phase, preferably of simulated counter-current type.

Thus, the present invention relates to a zeolite adsorbent comprising zeolite EMT crystals, which adsorbent comprises barium and/or potassium, in which the total content of alkali metal or alkaline-earth metal ion oxides other than BaO and $K_2O$ is less than 5%, preferably between 0 and 2% and advantageously between 0 and 1% by weight, limits included, relative to the total mass of the adsorbent.

The adsorbent advantageously comprises:
 barium
 or barium and potassium.

Preferably, the zeolite adsorbent is an adsorbent in which:
 a. the content of barium oxide (BaO) is greater than 10%, preferably greater than 15%, very preferably greater than 18%, more preferably greater than 23% and even more preferably greater than 33% by weight relative to the total mass of the adsorbent,
 b. the content of potassium oxide $K_2O$ is between 0 and 25%, preferably between 0 and 15%, more preferably between 0 and 5% and even more preferably between 0 and 2% by weight relative to the total mass of the adsorbent.

The zeolite EMT of the adsorbent of the present invention may be prepared in various ways. Suitable preparation procedures are especially described in the following papers: *Chem. Mater.* (2012), 24, 4758-4765; and *Science*, Jan. 2012, 335, 70-73. However, any method which makes it possible to obtain zeolite EMT, with or without organic structuring and with or without seeding, is also useable.

Preferably, the zeolite EMT has an Si/Al atomic ratio of between 1.00 and 2.00, limits included, preferably between 1.00 and 1.50, limits included, more preferably between 1.05 and 1.50, limits included, and even more preferably between 1.10 and 1.50, limits included. However, the invention does not exclude the adsorbent from containing mixtures of two or more types of zeolites EMT as have just been defined.

In the present document, the term "number-average diameter" or "size" is used for zeolite crystals and for zeolite agglomerates. The method for measuring these magnitudes is explained later in the description. The number-average diameter of the zeolite EMT crystals is advantageously between 5 nm and 1500 nm, preferably between 5 nm and 1000 nm and even more preferably between 10 nm and 500 nm, limits included.

The zeolite adsorbents according to the present invention thus comprise zeolite EMT crystals. The zeolite adsorbents according to the present invention may also contain crystals of other zeolites, chosen from zeolites of FAU structure, especially LSX, MSX, X or Y, EMC-1, or chosen from zeolites of LTA or MFI structure.

The zeolite adsorbents according to the present invention may also comprise zeolite phases of EMT-FAU intergrowth, such as the phases CSZ-1, ECR-30, ZSM-20 and ZSM-3, to mention but the main ones.

The adsorbents may also comprise a non-zeolite phase, i.e. a non-crystalline phase that is essentially inert towards adsorption.

The mass fraction of zeolite(s) EMT in the adsorbent according to the present invention may be at least 1% by weight of zeolite(s) EMT relative to the total weight of the adsorbent, preferably at least 10%, more preferably at least 20% and even more preferably at least 30%. In this case, the adsorbent also preferentially comprises another zeolite of faujasite structure.

The mass fraction of zeolite(s) EMT in the adsorbent according to the present invention may be at least 50% by weight of zeolite(s) EMT relative to the total weight of the adsorbent, preferably at least 80%, this mass fraction possibly ranging up to 100% and typically up to 99.5% by weight.

The zeolite adsorbent of the invention is preferably in the form of an agglomerate, i.e. it consists of zeolite crystals and of at least one non-zeolite phase which is an agglomeration binder enabling the cohesion of the crystals with each other. Thus, the zeolite adsorbent of the invention is referred to as an "agglomerate" in the rest of the present description.

According to yet another preferred embodiment of the invention, the zeolite adsorbent has a content of barium oxide (BaO) of between 23% and 40%, limits included, and typically between 33% and 40%, limits included, by weight relative to the total weight of the adsorbent.

According to a preferred embodiment, the zeolite adsorbent according to the invention has a loss on ignition, measured at 950° C. according to standard NF EN 196-2, of between 0 and 7.7%, preferably between 4.5% and 6.5% and advantageously between 4.8% and 6%, limits included.

The zeolite adsorbent according to the present invention preferentially has a mechanical strength generally greater than or equal to 1.8 MPa, typically greater than or equal to 2.1 MPa. This mechanical strength is measured by the Shell method series SMS1471-74 adapted for agglomerates less than 1.6 mm in size.

The adsorption capacity is itself measured by measuring the micropore volume of the adsorbent evaluated according to the t-plot method from the nitrogen ($N_2$) adsorption isotherm at a temperature of 77 K, after degassing under vacuum at 300° C. for 16 hours. The micropore volume of the zeolite adsorbents of the invention preferentially ranges from 0.100 $cm^3/g$ to 0.350 $cm^3/g$, preferably from 0.120 $cm^3/g$ to 0.350 $cm^3/g$ and more preferably from 0.140 $cm^3/g$ to 0.350 $cm^3/g$.

According to another aspect, the invention relates to a process for preparing zeolite agglomerates as have just been defined, which process comprises at least the steps of:
  a) agglomeration of crystals of at least one zeolite EMT and optionally of at least another zeolite with a binder,
  b) optionally zeolitization of the said binder by the action of an alkaline basic solution,
  c) cationic exchange of the agglomerate by placing in contact with a solution of barium ions, of potassium ions, or of barium ions and potassium ions,
  d) optional cationic exchange with potassium,
  e) followed by washing and drying of the product thus treated, and
  f) activation of the zeolite agglomerate.

The size of the zeolite EMT crystals used in step a) is measured by observation by scanning electron microscope (SEM) or by observation by transmission electron microscope (TEM). This SEM or TEM observation also makes it possible to confirm the presence of a non-zeolite phase comprising, for example, the binder or the residual binder not converted during the optional zeolitization step or any other amorphous phase in the agglomerates.

The agglomeration and the forming (step a) may be performed according to any technique known to those skilled in the art, such as extrusion, compacting, agglomeration, and the like. The proportions of agglomeration binder, which is optionally zeolitizable, (see the definition later) and of zeolite(s) used are typically those of the prior art, i.e. from 5 parts to 20 parts by weight of binder per 95 parts to 80 parts by weight of zeolite. The agglomerates derived from step a), whether they are in the form of beads, extrudates or the like, generally have a number-average diameter (or their largest dimension when they are not spherical) of between 0.2 mm and 2 mm, in particular between 0.4 mm and 0.8 mm and preferably between 0.4 mm and 0.65 mm, limits included.

After step a), the finest agglomerate particles may be removed by cycloning and/or screening and/or the excessively coarse particles may be removed by screening or crushing, for example in the case of extrudates.

The agglomeration binder used in step a) may be zeolitizable. It then contains preferably at least 80%, at least 90%, more preferably at least 95% and more particularly at least 96% by weight of zeolitizable clay and may also contain other mineral binders, such as bentonite, attapulgite and the like. The term "zeolitizable clay" means a clay or a mixture of clays that can be converted into zeolite material (i.e. active material for the purpose of adsorption), usually by the action of an alkaline basic solution. The zeolitizable clay generally belongs to the family of kaolins, kaolinites, nacrites, dickites, halloysite and/or meta-kaolins. Kaolin is preferred and is the one most commonly used.

Other clays, especially such as sepiolite or attapulgite, may also be used.

In all cases, the clays may be used in their raw form or may be subjected beforehand to one or more treatments chosen, for example, from calcination, treatment with acid, chemical modification, and the like.

The zeolite EMT powder used in step a) may be derived from the synthesis of zeolite(s) EMT crystals predominantly, or even exclusively, comprising sodium cations, for example zeolites NaEMT, but it would not constitute a departure from the scope of the invention to use a powder that has undergone one or more cationic exchanges, after its synthesis and before its use in step a).

During step a), besides the zeolite EMT powder and the binder, one or more additives may also be added, for example additives intended to facilitate agglomeration or to improve the hardening of the agglomerates formed, such as lignin, starch, carboxymethylcellulose and other additives known to those skilled in the art. Silica may also be added. The optional source of silica may be of any type known to a person skilled in the art, who is a specialist in the synthesis of zeolites, for example colloidal silica, diatomaceous earths, perlite, calcination ash (fly ash), sand, or any other form of solid silica.

After the drying in step a), calcination is performed at a temperature generally of between 500° C. and 600° C. When the forming is performed with a zeolitizable clay, this step makes it possible to transform the zeolitizable clay, typically kaolin, into meta-kaolin, which can thereafter be converted into zeolite during the zeolitization step (step b)). The principle thereof is outlined in "Zeolite Molecular Sieves" by D. W. Breck, John Wiley and Sons, New York (1973), pp. 314-315.

Zeolitization of the agglomeration binder is performed according to any method known to those skilled in the art and may be performed, for example, by immersion of the product of step a) in an alkaline basic solution, which is generally aqueous, for example aqueous sodium hydroxide and/or potassium hydroxide solution.

As a general rule, the concentration of the alkaline zeolitization solution is preferably between 0.5 M and 5 M. The zeolitization is preferably performed hot, at a temperature above room temperature, and typically at temperatures from about 80° C. to 100° C., for example between room temperature (i.e. about 20° C.) and the boiling point of the alkaline zeolitization solution. The duration of the zeolitization process is generally between a few tens of minutes and a few hours and preferably between about 1 hour and 8 hours.

Step c) of exchange with barium and/or potassium of the cations of zeolite EMT is performed according to the standard methods known to those skilled in the art, and usually by placing the agglomerates derived from step b) (or from step d)) in contact with a salt, such as barium chloride ($BaCl_2$) for exchange with barium and/or potassium chloride (KCl) for exchange with potassium, as an aqueous solution at a temperature between room temperature and 100° C. and preferably between 80° C. and 100° C. To obtain high barium oxide contents rapidly, i.e. preferably greater than 10% and more preferentially greater than 18% by weight relative to the total weight of the agglomerate, preferably greater than 23% by weight and more preferably ranging from 30% to 40% and advantageously ranging from 33% to 40% by weight relative to the total weight of the agglomerate, it is preferred to work with a large excess of barium ions relative to the cations of the zeolite that it is desired to exchange, typically an excess of the order of 10 to 12, advantageously by performing successive exchanges.

The optional exchange with potassium (step d)) may be performed before and/or after the exchange with barium (step c)). As indicated previously, it is also possible to agglomerate in step a) zeolite EMT powder already containing potassium ions (pre-exchange of the cations present in the starting zeolite EMT, typically sodium cations, with potassium ions before step a)) and to dispense with (or otherwise) step d).

Washing is then performed, generally and preferably with water, followed by drying of the agglomerate thus obtained.

The activation which follows the drying is performed in a conventional manner, according to the methods known to those skilled in the art, for example at a temperature generally between 100° C. and 400° C. and preferably between 200° C. and 300° C. This activation step e) has the aim of setting the water content and also the loss on ignition of the adsorbent optimally for the envisaged use. It is generally performed by thermal activation, which is preferentially implemented between 200° C. and 300° C. for a time determined as a function of the desired water content and the desired loss on ignition, typically from 1 to 6 hours.

The present invention also relates to the uses of the zeolite adsorbents described above as adsorption agents that can advantageously replace the adsorption agents described in the literature, based on zeolite X, comprising barium oxide, or based on zeolite X comprising barium oxide and potassium oxide, and especially in the uses listed below:

separation of aromatic C8 isomer fractions and especially of xylenes,
separation of substituted toluene isomers, such as nitrotoluene, diethyltoluene, toluenediamine, and the like,
separation of cresols,
separation of polyhydric alcohols, such as sugars.

The invention relates especially to a process for recovering high-purity para-xylene from aromatic isomer fractions containing 8 carbon atoms, which consists in using, as para-xylene adsorption agent, a zeolite adsorbent according to the invention, used in liquid-phase processes but also in gas-phase processes. The term "high-purity para-xylene" means a product that is suitable for use in the production of terephthalic acid or dimethyl terephthalate, i.e. a purity of at least 99.5% by weight, preferably at least 99.7% by weight, preferably at least 99.8% by weight and even more preferably at least 99.9% by weight. The para-xylene purity may be determined via chromatographic methods. A gas chromatography method that may be used both for determining the purity of para-xylene and the specific amounts of impurities is the ASTM D-3798 method.

It is thus possible to separate the desired product (para-xylene) by preparative adsorption liquid chromatography (batchwise), and advantageously continuously on a simulated mobile bed, i.e. in simulated counter-current mode or in simulated co-current mode, and more particularly in simulated counter-current mode.

The operating conditions of an industrial adsorption unit of simulated counter-current type are generally the following:
number of beds: 6 to 30,
number of zones: at least 4 functioning zones, each being located between a feed point and a withdrawal point,
temperature between 100° C. and 250° C. and preferably between 150° C. and 190° C.,
pressure of the industrial unit between the bubble pressure of xylenes at the process temperature and 3 MPa,
desorbent/feedstock flow rate ratio of between 0.7 and 2.5, for example between 0.9 and 1.8 for an adsorption-only (stand alone) unit and between 0.7 and 1.4 for an adsorption unit combined with a crystallization unit,
degree of recycling (i.e. the ratio of the average recycling rate (average of the rates of zones weighted by the number of beds per zone) to the feedstock flow rate) of between 2.5 and 12 and preferably between 3.5 and 6.

In this respect, reference may be made to the teaching of patents U.S. Pat. Nos. 2,985,589, 5,284,992 and 5,629,467.

The operating conditions of a simulated co-current industrial adsorption unit are generally the same as those functioning in simulated counter-current, with the exception of the degree of recycling, which is generally between 0.8 and 7. On this aspect, reference may be made to patents U.S. Pat. Nos. 4,402,832 and 4,498,991.

The desorption solvent may be any desorbent known to those skilled in the art and whose boiling point is below that of the feedstock, such as toluene, but also a desorbent whose boiling point is higher than that of the feedstock, such as para-diethylbenzene (PDEB). The selectivity of the adsorbents according to the invention for the adsorption of the para-xylene contained in aromatic C8 fractions is optimal when their loss on ignition measured at 900° C. is generally between 4.0% and 7.7% and preferably between 4.7% and 6.7%.

Characterization Techniques
Particle Size of the Crystals:
The estimation of the number-average diameter of the zeolite EMT crystals used in step a) and of the zeolite EMT crystals contained in the agglomerates is performed by scanning electron microscope (SEM) observation or by transmission electron microscope (TEM) observation.

In order to estimate the size of the zeolite crystals on the samples, a set of images is taken at a magnification of at least 5000. The diameter of at least 200 crystals is then measured using dedicated software, for example the Smile View software from the publisher LoGraMi. The accuracy is of the order of 3%.

Chemical Analysis of the Zeolite Adsorbents—Si/Al Ratio and Degree of Exchange:

An elemental chemical analysis of the final product obtained after steps a) to f) described previously may be performed according to various analytical techniques known to those skilled in the art. Among these techniques, mention may be made of the technique of chemical analysis by X-ray fluorescence as described in standard NF EN ISO 12677:2011 on a wavelength-dispersive spectrometer (WDXRF), for example the Tiger S8 machine from the company Brüker.

X-Ray fluorescence is a non-destructive spectral technique which exploits the photoluminescence of atoms in the X-ray range to establish the elemental composition of a sample. Excitation of the atoms, generally with an X-ray beam or by bombardment with electrons, generates specific radiations after the atom has returned to the ground state. The X-ray fluorescence spectrum has the advantage of depending very little on the chemical combination of the element, which affords a precise determination, both quantitative and qualitative. A measurement uncertainty of less than 0.4% by weight is conventionally obtained after calibration for each oxide.

These elemental chemical analyses make it possible both to check the Si/Al atomic ratio of the zeolite within the agglomerate and to check the quality of the ionic exchange described in step c) and in the optional step d). In the description of the present invention, the measurement uncertainty of the Si/Al atomic ratio is ±5%.

The quality of the ionic exchange is linked to the number of moles of sodium oxide, $Na_2O$, remaining in the zeolite agglomerate after exchange. More precisely, the degree of exchange with barium ions is estimated by evaluating the ratio of the number of moles of barium oxide, $BaO$, to the number of moles of the combination ($BaO+Na_2O$). Similarly, the degree of exchange with barium and potassium ions is estimated by evaluating the ratio of the number of moles of the barium oxide+potassium oxide combination ($BaO+K_2O$) to the number of moles of the combination ($BaO+K_2O+Na_2O$). It should be noted that the contents of various oxides are given as weight percentages relative to the total weight of the anhydrous zeolite adsorbent.

Particle Size of the Zeolite Adsorbents:

The determination of the number-average diameter of the zeolite adsorbents obtained after step a) of agglomeration and shaping is performed by analysis of the particle size distribution of an agglomerate sample by imaging according to standard ISO 13322-2:2006, using a conveyor belt enabling the sample to pass in front of the objective lens of the camera.

The number-average diameter is then calculated from the particle size distribution by applying standard ISO 9276-2:2001. In the present document, the term "number-average diameter" or "size" is used for zeolite agglomerates. The accuracy is of the order of 0.01 mm for the size range of agglomerates of the invention.

Mechanical Strength of the Zeolite Adsorbents:

The resistance to crushing of a bed of zeolite adsorbents as described in the present invention is characterized according to the Shell method series SMS1471-74 (Shell Method Series SMS1471-74, "Determination of Bulk Crushing Strength of Catalysts. Compression-Sieve Method"), in association with the "BCS Tester" machine sold by the company Vinci Technologies. This method, initially intended for the characterization of catalysts from 3 mm to 6 mm, is based on the use of a 425 µm screen which makes it possible especially to separate out the fines created during crushing. The use of a 425 µm screen remains suitable for particles with a diameter of greater than 1.6 mm, but should be adapted according to the particle size of the agglomerates that it is desired to characterize.

The agglomerates of the present invention, generally in the form of beads or extrudates, generally have a number-average diameter or a length, i.e. largest dimension in the case of non-spherical agglomerates, of between 0.2 mm and 2 mm, better still between 0.4 mm and 2 mm, in particular between 0.4 mm and 0.8 mm and preferably between 0.4 mm and 0.65 mm. Consequently, a 200 µm screen is used instead of the 425 µm screen mentioned in the standard Shell method SMS1471-74.

The measurement protocol is as follows: a sample of 20 $cm^3$ of agglomerated adsorbents, screened beforehand with the appropriate screen (200 µm) and predried in an oven for at least 2 hours at 250° C. (instead of the 300° C. mentioned in the standard Shell method SMS1471-74), is placed in a metal cylinder of known internal cross section. An increasing force is imposed in stages on this sample by means of a piston, through a bed of 5 $cm^3$ of steel balls so as to better distribute the force exerted by the piston on the adsorbent agglomerates (use of balls 2 mm in diameter for particles of spherical shape with a diameter strictly below 1.6 mm). The fines obtained at the various pressure stages are separated out by screening (appropriate 200 µm screen) and weighed.

The bed crushing strength is determined by the pressure in megaPascals (MPa) for which the amount of cumulative fines passing through the screen is 0.5% by weight of the sample. This value is obtained by plotting on a graph the mass of fines obtained as a function of the force applied to the adsorbent bed and by interpolating to 0.5% by mass of cumulative fines. The mechanical bed crushing strength is typically between a few hundred kPa and a few tens of MPa and generally between 0.3 MPa and 3.2 MPa. The accuracy is conventionally less than 0.1 MPa.

Determination of the Zeolite Fractions of the Zeolite Adsorbents:

The nature and amount of the various zeolite fractions are determined by X-ray diffraction analysis, known to those skilled in the art by the abbreviation XRD. This analysis is performed on a Brüker brand machine and then the amount of zeolite fractions is evaluated using the TOPAS software from the company Brüker.

Micropore Volume:

The crystallinity of the agglomerates is also evaluated by measuring their micropore volume while comparing it with that of a suitable reference (100% crystalline zeolite under identical cationic treatment conditions or theoretical zeolite). This micropore volume is determined from the measurement of the adsorption isotherm of a gas, such as nitrogen, at its liquefaction temperature. Prior to the adsorption, the zeolite adsorbent is degassed between 300° C.-450° C. for a time of 9 hours to 16 hours, under vacuum ($P<6.7\times10^{-4}$ Pa). The measurement of the nitrogen adsorption isotherm at 77 K is then performed on an ASAP 2010 M machine from Micromeritics, taking at least 35 measurement points at relative pressures having a ratio $P/P_0$ of between 0.002 and 1. The micropore volume is determined according to the t-plot method from the isotherm obtained, by applying standard ISO 15901-3:2007. The t-plot is the diagram representing the adsorbed volume as a function of the thickness t of multilayer calculated by the Harkins-Jura equation. The micropore volume is obtained from the intersection with the y-axis of the linear regression obtained on the t-plot for thickness values t of between 0.35 and 0.5 nm. The micropore volume evaluated by the t-plot method is expressed in $cm^3$ of liquid adsorbate per gram of adsorbent. The measurement uncertainty is ±0.003.

Loss on Ignition of the Zeolite Adsorbents:

The loss on ignition is determined under an oxidizing atmosphere, by calcination of the sample in air at a temperature of 950° C.±25° C., as described in standard NF EN 196-2 (April 2006). The measurement standard deviation is less than 0.1%.

Characterization of the Adsorption in the Liquid Phase by Breakthrough:

The technique used for characterizing the adsorption of molecules in the liquid phase on a porous solid is the "breakthrough" technique described by Ruthven in "Principles of Adsorption and Adsorption Processes" (Chapters 8 and 9, John Wiley & Sons, 1984), which defines the technique of breakthrough curves as the study of the response to the injection of an echelon of adsorbable constituents. Analysis of the average output time (first moment) of the breakthrough curves yields information regarding the amounts adsorbed and also makes it possible to evaluate the selectivities, i.e. the separation factor, between two adsorbable constituents (equation 9.9). The injection of a non-adsorbable constituent used as tracer is advisable for the estimation of non-selective volumes. The analysis of the dispersion (second moment) of the breakthrough curves makes it possible to evaluate the equivalent height of theoretical plates, based on the representation of a column by a finite number of ideally stirred hypothetical reactors (theoretical stages), which is a direct measurement of the axial dispersion and of the matter transfer resistance of the system.

EXAMPLES

Example A

Synthesis of Zeolite EMT Crystals

A gel having the molar composition 18.45 $Na_2O$-5.15 $SiO_2$—$Al_2O_3$ 240 $H_2O$ is prepared by mixing the following reagents: sodium silicate, sodium aluminate, sodium hydroxide and demineralised water. The gel is matured at 0° C. for 5 minutes with stirring. Crystallization is performed in a closed reactor with stirring for 34 hours at 30° C.

Recovery is performed by centrifugation. The reaction product is first centrifuged once to remove the mother liquors (10 000 revolutions per minute for 10 minutes). The solid obtained is washed by reslurrying with demineralised water, and then centrifuged under the same conditions. This operation is repeated until the pH of the washing liquors is less than 8. The solid is then dried overnight at 100° C. in air. The crystals obtained are identified by X-ray diffraction (XRD analysis) as being zeolite EMT crystals. Chemical analysis of the solid gives an Si/Al atomic ratio=1.2. The micropore volume evaluated according to the t-plot method as described in the technical characterization section and expressed in $cm^3$ per gram of dry adsorbent is 0.14±0.003 $cm^3$/g. Analysis of the size of the zeolite crystals is performed by transmission electron microscopy and shows that their number-average diameter is about 20 nm.

Preparation of the Zeolite Adsorbents

Example 1

Shaping by Pelletizing/Crushing

Agglomerates were prepared from the crystals synthesized (powder) in Example A. The powder is first shaped by compacting into pellets. The pellets are then ground and the crushed agglomerates obtained are screened so as to retain those whose particle size is between 0.25 mm and 0.5 mm.

Example 2

Shaping by Extrusion/Crushing

A homogeneous mixture is prepared and 500 g of crystals of zeolite NaEMT prepared according to the procedure described in Example A are agglomerated with 110 g of attapulgite (expressed as calcined equivalent) with the amount of water that enables extrusion of the mixture. The extrudates are dried, crushed so as to recover grains with a number-average diameter equal to 0.7 mm, and then calcined at 550° C. under a stream of nitrogen for 2 hours.

Example 3

Shaping by Extrusion/Crushing and Zeolitization of the Binder

A homogeneous mixture is prepared and 850 g of crystals of zeolite NaEMT prepared according to the procedure described in Example A are agglomerated with 150 g of kaolin and 30 g of colloidal silica sold under the trade name Klebosol®30 (containing 30% by weight of $SiO_2$ and 0.5% of $Na_2O$) with the amount of water that enables extrusion of the mixture. The extrudates are dried, crushed so as to recover grains with a number-average diameter equal to 0.7 mm, and then calcined at 550° C. under a stream of nitrogen for 2 hours.

300 g of agglomerates obtained are placed in a glass reactor equipped with a jacket regulated at a temperature of between 80° C. and 100° C., 2.5 L of aqueous sodium hydroxide solution of concentration 2.5 M are then added and the reaction medium is stirred for a time of between 1 hour and 10 hours.

Washing of the agglomerates is then performed in 3 successive operations of washing with water followed by emptying of the reactor. The efficacy of the washing is ensured by measuring the final pH of the washing liquors, between 10.0 and 10.5.

Example 4

Cationic Exchange with Barium

The sodium cations of the agglomerates obtained in Example 1, 2 or 3 are exchanged with barium ions by means of an aqueous 0.5 M barium chloride solution at 95° C. in 4 steps. In each step, the volume ratio of solution to the mass of solid is 20 mL/g and the exchange is continued for 3 hours each time. Between each exchange, the solid is washed several times so as to free it of the excesses of salt. The agglomerates are then dried at 80° C. for 2 hours and finally activated at 250° C. for 2 hours under a stream of nitrogen.

The loss on ignition, measured as described previously, is 5.4%±0.1% for each sample. The degree of barium exchange of the agglomerates calculated from the elemental analyses of the barium and sodium oxides by X-ray fluorescence as described in the characterization techniques is 99.7±0.2%.

Example 5

Cationic Exchange with Barium and Potassium

The sodium cations of the agglomerates obtained in Example 1, 2 or 3 are exchanged with barium and potassium cations using an aqueous 1.35 M potassium chloride and 0.35 M barium chloride solution at 95° C. in 4 steps. In each step, the volume ratio of solution to the mass of solid is 20 mL/g and the exchange is continued for 3 hours each time. Between each exchange, the solid is washed several times so as to free it of the excesses of salt. The agglomerates are then dried at 80° C. for 2 hours and finally activated at 250° C. for 2 hours under a stream of nitrogen.

The loss on ignition, measured as described previously, is 5.6%±0.1% for each sample. The degree of barium+potassium exchange of the agglomerates calculated from the elemental analyses of the barium and sodium oxides by X-ray fluorescence as described in the characterization techniques is 99.7±0.2%. The K/Ba atomic ration is 0.9±0.1.

Example 6

Breakthrough Test

A breakthrough test (frontal chromatography) is then performed on the agglomerates obtained in Example 4 to evaluate their efficacy. The amount of adsorbent used for this test is about 30 g.

The procedure for obtaining the breakthrough curves is the following:
  Filling of the column via the screen and inserting in the test bed.
  Filling with the solvent at room temperature.
  Gradual raising to the absorption temperature under a stream of solvent (5 cm³/min).
  Injection of solvent at 5 cm³/min when the absorption temperature is reached.
  Solvent/feedstock switching to inject the feedstock (5 cm³/min).
  The injection of the feedstock is then maintained for a time sufficient to reach thermodynamic equilibrium.
  Collection and analysis of the breakthrough effluent.

The pressure is sufficient for the feedstock to remain in the liquid phase, i.e. 1 MPa. The absorption temperature is 175° C. The composition of the feedstock is as follows:
  para-xylene: 22% by weight
  meta-xylene: 22% by weight
  ortho-xylene: 22% by weight
  ethylbenzene: 22% by weight
  isooctane: 12% by weight (this is used as a tracer for estimating the non-selective volumes and does not take part in the separation)

The binary selectivities for para-xylene relative to the other compounds are calculated from the adsorbed amounts of each compound, these amounts being determined by material balance from the first moments of the breakthrough curves of all of the constituents present in the effluent. The results are collated in Table 1 below:

TABLE 1

| PX/MX selectivity | PX/OX selectivity | PX/EB selectivity |
|---|---|---|
| 2.0 | 2.0 | 1.8 |

PX: para-xylene,
MX: meta-xylene,
OX: ortho-xylene,
EB: ethylbenzene

The results thus show selectivity in favour of para-xylene. The separation factors with respect to meta-xylene, ortho-xylene or ethylbenzene are similar. Consequently, this adsorbent may advantageously be used for selectively absorbing para-xylene irrespective of the composition of the mixture to be separated, and especially in the case of a mixture comprising a large fraction of ethylbenzene.

The invention claimed is:

1. A zeolite adsorbent comprising zeolite EMT crystals and comprising barium and/or potassium, in which the total content of alkali metal or alkaline-earth metal ion oxides other than barium oxide BaO and potassium oxide $K_2O$ is between 0 and 5%, limits included, relative to the total mass of the adsorbent.

2. The zeolite adsorbent according to claim 1, also comprising a non-zeolite phase.

3. The zeolite adsorbent according to claim 1, wherein the zeolite EMT crystals have an Si/Al atomic ratio of between 1.00 and 2.00, limits included.

4. The zeolite adsorbent according to claim 1, wherein the number-average diameter of the zeolite EMT crystals is between 5 nm and 1500 nm, limits included.

5. The zeolite adsorbent according to claim 1, which also comprises crystals of at least one other zeolite, selected from the group consisting of zeolites of FAU structure, zeolites of LTA structure, and zeolites of MFI structure.

6. The zeolite adsorbent according to claim 5, wherein the said at least one other zeolite is selected from the group consisting of zeolites of faujasite structure, alone or as a mixture and wherein the mass fraction of zeolite EMT is between 1% and 50%.

7. The zeolite adsorbent according to claim 1, wherein the mass fraction of zeolite EMT is greater than 50% relative to the total weight of adsorbent.

8. The zeolite adsorbent according to claim 1, comprising zeolite phases of EMT-FAU intergrowth.

9. The zeolite adsorbent according to claim 1, wherein:
  the barium content (expressed as a weight percentage of barium oxide BaO) is greater than 10% by weight relative to the total mass of the adsorbent, limits included,
  the potassium content (expressed as a weight percentage of potassium oxide $K_2O$) is between 0 and 25% by weight relative to the total mass of the adsorbent.

10. The zeolite adsorbent according to claim 1, wherein the zeolite adsorbent has a loss on ignition, measured at 950° C. according to standard NF EN 196-2, of between 0 and 7.7% by weight.

11. The zeolite adsorbent according to claim 1, wherein the zeolite adsorbent has a number-average diameter of between 0.2 mm and 2 mm, limits included.

12. A process for preparing a zeolite adsorbent according to claim 1, comprising at least the steps of:
  a) agglomerating a zeolite powder comprising zeolite EMT with a binder and forming, followed by drying and calcination, to obtain an agglomerate, c) performing cationic exchange of the agglomerate by placing the agglomerate in contact with a solution of barium ions, or of potassium ions, or of barium ions and potassium ions,
d) optionally, exchanging with potassium,
e) followed by washing and drying of the product thus treated, and
f) activating the zeolite adsorbent thus obtained.

13. The process according to claim 12, wherein step a) uses a binder containing at least 80% by weight of zeolitizable clay and a source of silica and the process comprises a step b) of zeolitization of the said binder by the action of an alkaline basic solution.

14. A zeolite adsorbent obtained according to the process of claim 12.

15. A process using an adsorbent, wherein the adsorbent is a zeolite adsorbent in accordance with claim 1 and the process is selected from the group consisting of:
separation of aromatic C8 isomer fractions,
separation of substituted toluene isomers,
separation of cresols, and
separation of polyhydric alcohols.

16. The process according to claim 15, wherein the process is the separation of para-xylene from aromatic isomer fractions containing 8 carbon atoms.

17. A process for recovering para-xylene from aromatic hydrocarbon isomer fractions containing 8 carbon atoms, in the liquid phase, by adsorption of para-xylene using a zeolite adsorbent in accordance with claim 1 in the presence of a desorbent.

18. The process for recovering para-xylene according to claim 17, wherein the process is a simulated mobile bed process.

19. A process for recovering para-xylene from aromatic hydrocarbon isomer fractions containing 8 carbon atoms, in the gas phase, by adsorption of para-xylene using a zeolite adsorbent in accordance with claim 1 in the presence of a desorbent.

20. A process for separating polyhydric alcohols using an adsorbent, wherein the adsorbent is a zeolite adsorbent in accordance with claim 1.

21. A process for separating substituted toluene isomers using an adsorbent, wherein the adsorbent is a zeolite adsorbent in accordance with claim 1.

22. A process for separating cresols using an adsorbent, wherein the adsorbent is a zeolite adsorbent in accordance with claim 1.

* * * * *